United States Patent

Sayed et al.

Patent Number: 5,693,948
Date of Patent: Dec. 2, 1997

[54] ADVANCED CCD-BASED X-RAY IMAGE SENSOR SYSTEM

[75] Inventors: Alaa A. Sayed, Concord; Daniel P. Laxson, Mountain View, both of Calif.

[73] Assignee: Loral Fairchild Corporation, Syosset, N.Y.

[21] Appl. No.: 561,436

[22] Filed: Nov. 21, 1995

[51] Int. Cl.⁶ ........................................ G01T 1/24
[52] U.S. Cl. ........................ 250/370.09; 378/98.8
[58] Field of Search ................ 250/370.09, 370.08, 250/371; 378/98.8; 377/62

[56] References Cited

U.S. PATENT DOCUMENTS

| | | | |
|---|---|---|---|
| 4,142,109 | 2/1979 | Knauer | 377/62 |
| 4,179,100 | 12/1979 | Sashin et al. | 250/416 |
| 4,366,382 | 12/1982 | Kotowski | 378/57 |
| 4,426,721 | 1/1984 | Wang | 378/99 |
| 4,901,336 | 2/1990 | Nishiki | 378/98.8 |
| 4,996,413 | 2/1991 | McDaniel et al. | 250/208 |
| 5,008,547 | 4/1991 | Molteni et al. | 250/368 |
| 5,037,207 | 8/1991 | Tomei et al. | 356/444 |
| 5,113,077 | 5/1992 | Shimizu et al. | 250/370.11 |
| 5,140,162 | 8/1992 | Stettner | 250/370.09 |
| 5,142,557 | 8/1992 | Toker et al. | 378/98.8 |
| 5,151,588 | 9/1992 | Kiri et al. | 250/208.1 |
| 5,331,166 | 7/1994 | Yamamoto et al. | 250/370.11 |
| 5,331,961 | 7/1994 | Inaba et al. | 128/659 |
| 5,340,988 | 8/1994 | Kingsley et al. | 250/370.09 |
| 5,434,418 | 7/1995 | Schick | 250/370.11 |
| 5,454,022 | 9/1995 | Lee et al. | 378/98.8 |
| 5,572,566 | 11/1996 | Suzuki et al. | 378/98.8 |

FOREIGN PATENT DOCUMENTS

| | | |
|---|---|---|
| 0 486 102 A1 | 5/1992 | European Pat. Off. . |
| 0 487 108 A1 | 5/1992 | European Pat. Off. . |
| WO 93/23952 | 11/1993 | WIPO . |

OTHER PUBLICATIONS

"Large format, high resolution image sensors", Morley M. Blouke et al., Optical Engineering, Sep. 1987, vol. 26, No. 9, pp. 837–843.

FLEX 8000 Programmable Logic Device Family, Data Sheet, Aug. 1994, ver. 4, Altera Corporation, San Jose, California, pp. 1–21 and 64.

*Primary Examiner*—Michael J. Tokar
*Assistant Examiner*—Richard Hanig
*Attorney, Agent, or Firm*—Perman & Green, LLP

[57] ABSTRACT

An improved CCD-based x-ray image sensor system enables the use of an uncooled or only slightly cooled CCD array (18a) within a standard size x-ray film cassette (1). The sensor system provides a number of advanced functions such as remote diagnostic capability, variable image resolution, real-time exposure control, automatic x-ray detection, a low-power "sleep" mode, and automatic, closed loop optimization of image quality.

20 Claims, 9 Drawing Sheets

ADVANCED CCD-BASED X-RAY IMAGE SENSOR SYSTEM

FIELD OF THE INVENTION

This invention relates generally to imaging devices and, in particular, relates to x-ray images sensors that employ a charge-coupled-device (CCD) readout device.

BACKGROUND OF THE INVENTION

The use of photodetectors as sensors of fluorescent radiation emitted by an x-ray responsive material are known in the art. By example, U.S. Pat. No. 4,996,413, entitled "Apparatus and Method For Reading Data From an Image Detector" by McDaniel et al., describes an n x m array of photodetectors (a non-CCD, MOS-type imager). Image information is read-out by sequentially selecting groups of rows starting with a row near the middle of the array and then sequentially selecting other groups of rows on alternative sides of the array middle. In this system an image processor 28 is said to produce a brightness control signal which is fed to an exposure control circuit 34 to regulate an x-ray tube power supply 16 and thereby the x-ray exposure (col. 3, lines 24–27).

The use of a charge coupled device (CCD) to record light emitted from a phosphor screen in response to x-rays is also known in the art. By example, in U.S. Pat. No. 5,142,557, entitled "CCD And Phosphor Screen Digital Radiology Apparatus And Method For High Resolution Mammography", by Toker et al., describes a CCD camera 20 having a cooled CCD array and a MIN-R phosphor screen 4. FIG. 5 of this patent shows an embodiment where a fiber optic reducer 45 is placed between the phosphor screen 4 and the CCD camera 20. FIG. 6 shows a parallel CCD array 61 and a CCD serial register 62. During an exposure clocks to the parallel array 61 are stopped, while serial register 62 is clocked and read-out to monitor the accumulated light exposure. A computer 65 generates a signal to terminate the x-ray dose as soon as a certain minimum acceptable threshold dosage is received (col. 9, line 16 to col. 10, line 37). An externally generated signal is required to indicate that the exposure has begun (col. 9, line 67 to col. 10, line 1).

The dark current density of conventional CCDs at room temperature has traditionally required that the CCD array be cooled during use, as in the foregoing Toker et al. patent. However, when used with tapered fiber bundles, even a moderately low profile thermoelectric (TE) cooled CCD array increases the vertical dimension of the sensor assembly by some significant amount. Another problem associated with TE coolers is that there tends to be a large heat load to remove from the back surface of the CCD focal plane assembly. As such, the requirement to also cool the CCD array to reduce the dark current complicates the use of CCDs with conventional x-ray machines.

In U.S. Pat. No. 5,331,166, entitled "Dental X-ray Image Detecting Device With an Automatic Exposure Function" by Yamamoto et al., there is described a medical x-ray image detecting device that includes an x-ray intensity detecting element that is located in a casing adjacent to an x-ray image sensor. The image sensor further includes a CCD device located on a ceramic substrate, and glass fiber bundles disposed between the CCD and an x-ray fluorescent element.

In general, these and other conventional x-ray image detecting systems are limited in both functionality and programmability.

By example, the saturation voltage of CCD devices may vary between 200 mv to 300 mv. If the CCD support electronics is optimized for operation at one saturation voltage (e.g., 300 mv), then a 200 mv device may deliver only two thirds of the dynamic range of a 300 mv device. It may thus be required to either accept the reduced dynamic range, or to reject the 200 mv device and replace same with a device having a higher dynamic range. However, the first alternative results in a reduction in imaging system capability, while the second alternative results in increased cost.

OBJECTS OF THE INVENTION

It is an object of this invention is to provide an improved CCD-based x-ray image sensor system that enables the use of an uncooled or only slightly cooled CCD array, the sensor system providing a number of advanced functions including, but not limited to, remote diagnostic capability, variable image resolution, real-time exposure control, automatic x-ray detection, a low-power "sleep" mode, and automatic remote optimization of image quality.

It is another object of this invention is to provide a CCD-based x-ray image sensor system having a number of advanced functions including, but not limited to, remote diagnostic capability, variable image resolution, real-time exposure control, automatic x-ray detection, a low-power "sleep" mode, and automatic, closed loop optimization of image quality.

SUMMARY OF THE INVENTION

The foregoing and other problems are overcome, and the objects of the invention are realized, by a CCD-based x-ray image sensor system that is constructed and operated in accordance with this invention.

In accordance with a first aspect of this invention, a CCD chip has serial readout registers at both the top and the bottom of a pixel array, and a test pattern is electrically injected by a test pattern generator into one of the horizontal serial registers from, by example, a reset drain (VRD) node of an output amplifier. The resulting charge packets are clocked into and through the CCD array and out through another horizontal serial register. The output charge packets are then digitized by an associated A/D converter 42 and output to an external controller for evaluation of the CCD performance.

A further aspect of this invention is the use of an automatic exposure, also referred to as a pre-scan or low-dose preview technique. This technique makes use of the binning capability of the CCD chip, and involves applying a low dose of x-rays and then summing a predetermined number of resulting low-level charge packets from a selected plurality of CCD pixels. From the magnitude of the charge obtained from the summation a controller is enabled to determine a maximum x-ray dose that will be required to obtain an adequate image. This technique beneficially avoids exposing a patient to a normal dose of x-rays, determining that the dose was inadequate, and then exposing the patient to another, possibly larger dose.

Another aspect of this invention is a real-time exposure control or tracking function. In this mode of operation the photoresponsive horizontal serial registers are clocked periodically during the exposure so as to determine an amount of signal coming into the serial registers. Based on the output signals the controller predicts when the optimum exposure time is reached, and the x-ray machine is then signalled to turn off at that time.

A further aspect of this invention is referred to as a variable resolution function which provides the CCD image sensor with a wide range of selectable effective pixel sizes and aspect ratios.

A further aspect of this invention is automatic x-ray detection. When operating in this mode, and while waiting for an exposure to commence, the CCD vertical clocks are run to continuously flush out a dark current signal. By also running the horizontal register clocks and by monitoring the output of the horizontal shift registers, a sudden increase in signal level, resulting from the onset of the exposure, is detectable and is correlated with the start of the exposure. The vertical clocks can then be immediately stopped to accumulate charge during the exposure, without experiencing any significant image degradation. At this time the horizontal clocks can be continued for performing the real time exposure control that was referred to above, and/or to detect an absence of x-rays at the end of the exposure. The automatic x-ray detection function is preferably accomplished by binning the charge resulting from after-scan clock cycles from the horizontal shift registers to obtain a large enough signal to accurately detect the onset of the exposure.

A further aspect of this invention operates the CCD chip and the associated electronics in a low-power or quiescent standby mode. This minimizes the dark signal and therefore the noise floor for a given readout time. The CCD chip and associated electronics are brought out of the low-power quiescent mode upon a detection of an activity that is a precursor to an x-ray exposure. The dark current is then flushed before the start of the exposure. In the low-power mode the CCD chip may be scanned at a lower clock rate, or not scanned at all.

A still further aspect of this invention is an ability to remotely perform an automatic optimization of image quality. This function is accomplished in a closed-loop manner by inputting data that specifies clock duty cycles, clock levels, and dc-bias potentials, and by sensing an output of the CCD sensor system in response to the specified parameters. Based on the output of the CCD chip for a given combination of clock bias and duty cycles, and also dc-bias potentials, the controller (which may be situated either locally or remotely) is enabled to determine optimal settings for such parameters as: (a) lowest dark signal (optimum MPP (multi-pinned phase)), (b) best vertical transfer efficiency, (c) best horizontal transfer efficiency, etc. These settings can be stored for subsequent use, and then downloaded to the CCD sensor system from a remote location.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
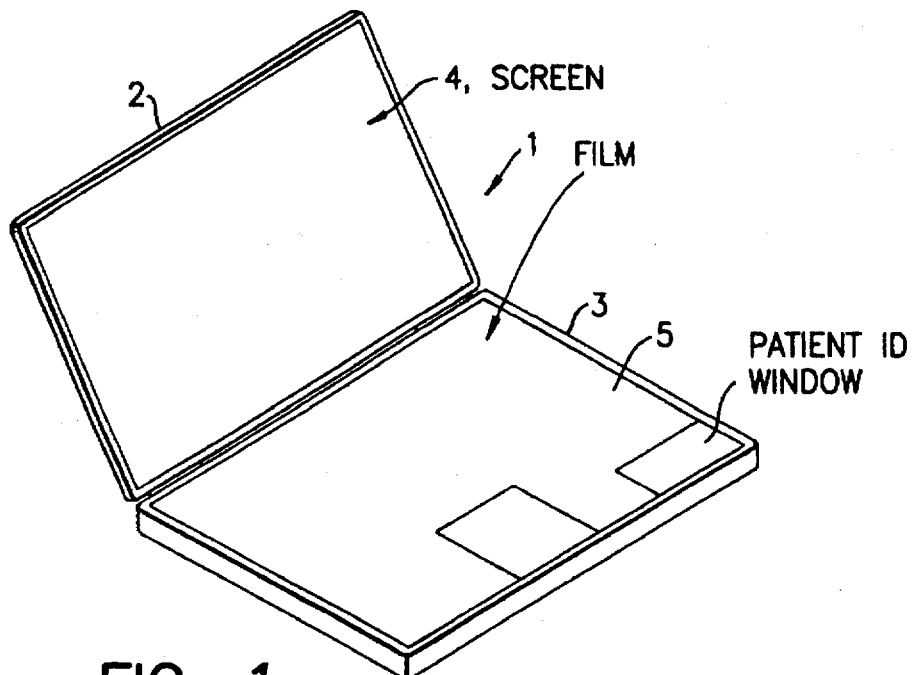
FIG. 1 is an elevational view showing a conventional x-ray film cassette in an opened position.

FIG. 1 is an elevational view of a conventional x-ray film cassette 1 of a type used for mammography. The cassette 1 has a hinged top cover 2 and a bottom portion 3. The top cover 2 includes a screen 4 that is responsive to x-rays for converting at least a portion thereof into light, typically ultraviolet or visible light, which then sensitizes a photographic film 5. Conventional screens 4 use a phosphor such as $CaWO_4$, a broad-band emitter in the uv-blue region of the spectrum, although some rare-earth-activated phosphors allow the x-ray dose to be reduced by at least a factor of four.

During use the top cover 2 is closed, and an object to be x-rayed is interposed between the outer surface of the top cover and a source of x-rays. Those x-rays that are not absorbed within the object pass through the top cover and impinge on the screen 4. The screen 4 converts (ideally) all of the impinging x-rays to light which then exposes the film 5. The cassette 1, when closed, has the approximate dimensions of 10.5×7.7×0.6 inches.

This invention provides an advanced CCD-based x-ray image sensor having a plurality of externally-controlled functions, and that is furthermore capable of being contained within the dimensions of the conventional cassette 1.

Figure 2:
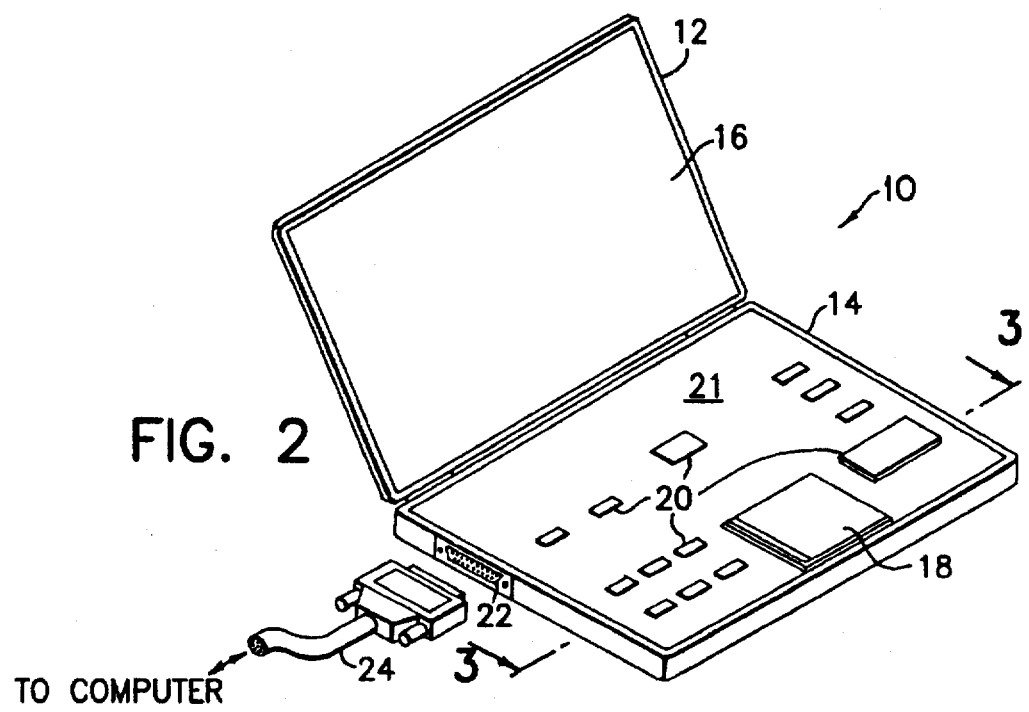
FIG. 2 is an elevational view illustrating an electronic x-ray cassette of this invention in an opened position.

Reference is now made to FIG. 2 for showing an elevational view of an embodiment of a low profile electronic cassette 10 that includes the electronic circuitry and functions in accordance with this invention. The cassette 10 is shown in an opened position, wherein a hinged top cover is separated from a lower cover 14. The top cover 12 has an inner surface 16 and is substantially transparent to x-rays having energies employed for conventional diagnostic purposes, such as those used in mammography applications. One suitable material for at least the top cover 12 is a carbon fiber based material. In this embodiment the lower cover 14 encloses a circuit board 21 that supports a screen/fiber optic/CCD (SFOCCD) assembly 18. This is considered to be a small field embodiment, and the top, x-ray responsive surface area of the SFOCCD assembly 18 has linear dimensions of approximately 6 cm×6 cm. The circuit board 21 also has mounted thereon a plurality of SFOCCD assembly support circuits 20 and a standard D shell-type connector 22 that interfaces to one end of an interface cable 24. A second end of the cable 24 is coupled to a computer (not shown in FIG. 2), as will be described in further detail below.

Figure 3:
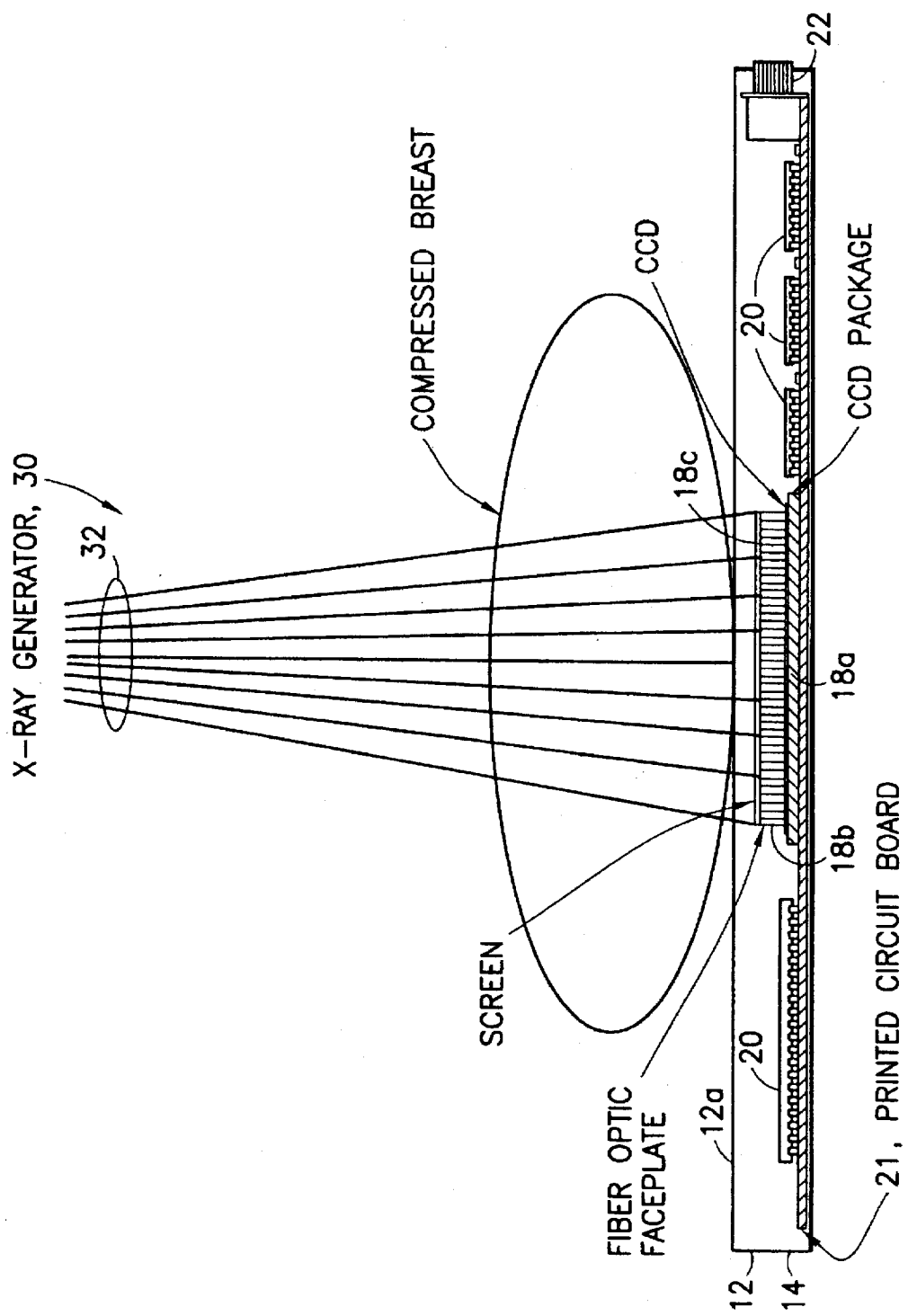
FIG. 3 is a cross-sectional view of the electronic x-ray cassette of FIG. 2 in a closed position when installed within an x-ray machine.

FIG. 3 illustrates a cross-sectional view of the electronic cassette 10 taken along the section line 3—3 of FIG. 2, and with the top cover 12 closed and the cassette 10 installed within an x-ray machine having an x-ray generator 30 providing an x-ray beam 32. An object to be x-rayed, in this case a breast, is positioned over a top surface 12a of the top cover 12. The breast is compressed against or over the top cover 12a in accordance with conventional practice, and is positioned such that it lies between the beam 32 and the top surface of the SFOCCD assembly 18.

The SFOCCD assembly 18 is comprised of a large area CCD sensor chip 18a, over which is bonded a fiber optic faceplate 18b, over which is bonded an x-ray sensitive screen 18c or to which is applied an x-ray sensitive material.

In this embodiment the SFOCCD assembly 18 has an active area bounded by sides of approximately 60 mm×60 mm. The CCD sensor chip 18a internally provides a 4 k×4 k array of 15×15 micron pixels, which can be combined on chip though pixel binning operations to provide, by example, an effective 2 k×2 k array of 30×30 micron pixels or an effective 1 k×1 k array of 60×60 micron pixels. The CCD sensor chip 18a is capable of operation in the MPP low-dark-current mode, and employs a three phase clock that transitions, nominally, between approximately −10 V and +5 V. The clock generation and biasing aspects of this invention are described in further detail below.

Figure 5:
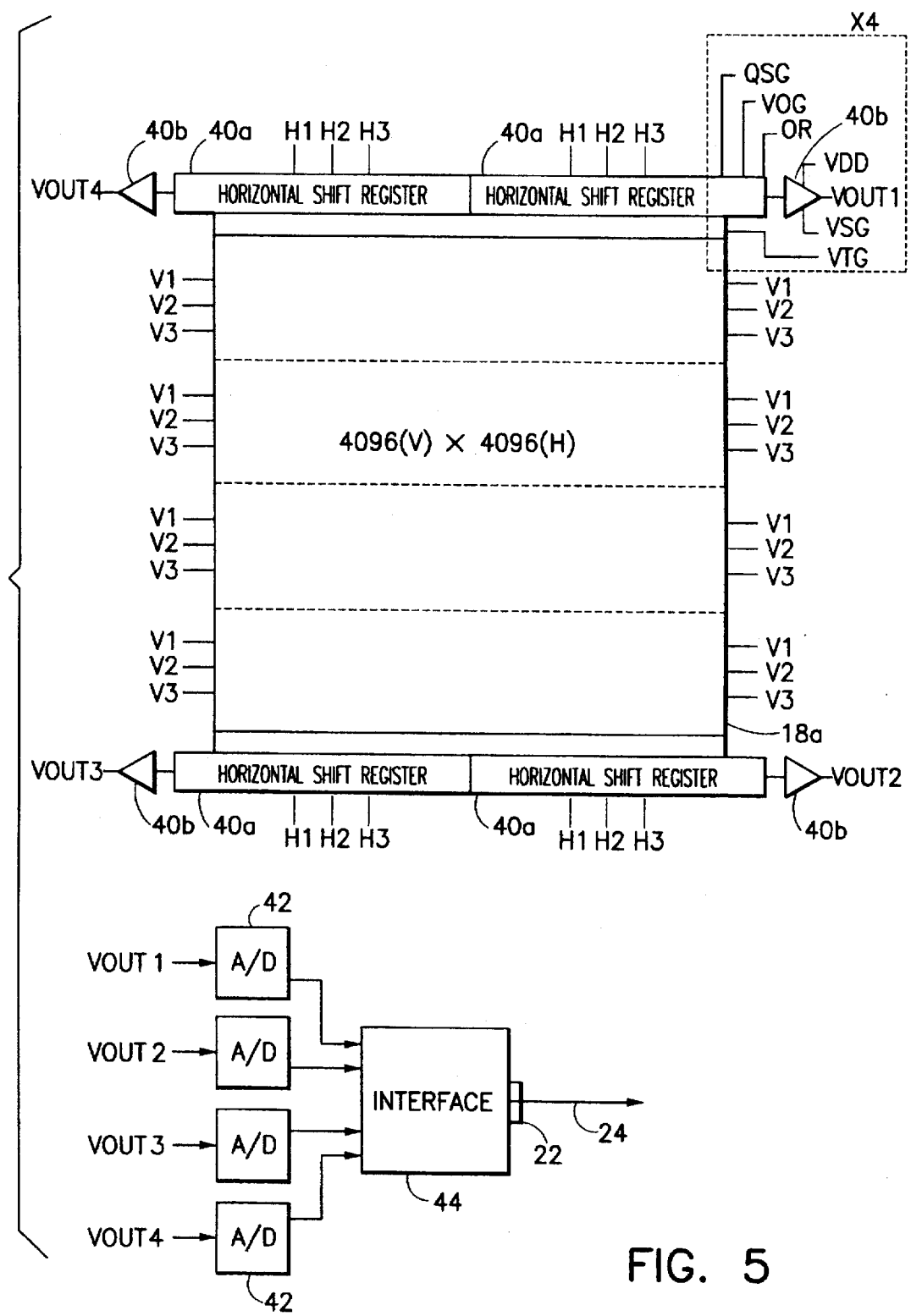
FIG. 5 is a schematic diagram of a CCD sensor chip that is suitable for use in practicing this invention.

Referring also now to FIG. 5, in a presently preferred embodiment the CCD sensor chip 18a is electrically differentiated into quadrants. Each quadrant has an associated horizontal shift register 40a and a low noise amplifier 40b for reading out of the CCD sensor chip 18a the photo-induced charge resulting from the conversion of x-rays into visible light in the screen 18c. The shift registers 40a are controlled by three phase horizontal clocks (H1–H3). The use of multiple output amplifiers 40b enables the charge to be read out a high speed, thereby reducing the effect of any dark currents generated after an x-ray exposure (it being realized that the CCD sensor chip 18a may not be cooled to cryogenic temperatures, but may instead be operated at ambient or slightly below ambient temperature). The outputs of the amplifiers 40b are input to associated A/D converters 42. Each of the A/D converters 42 provides a 12-bit digital representation of the voltage corresponding to the accumulated charge Within individual ones of the CCD pixels. The outputs of the A/D converters 42 are provided to a suitable interface device, in this case a VDU interface device 44, which outputs the A/D converter signals via the connector 22 and cable 24 to the external data processor.

Figure 8A:
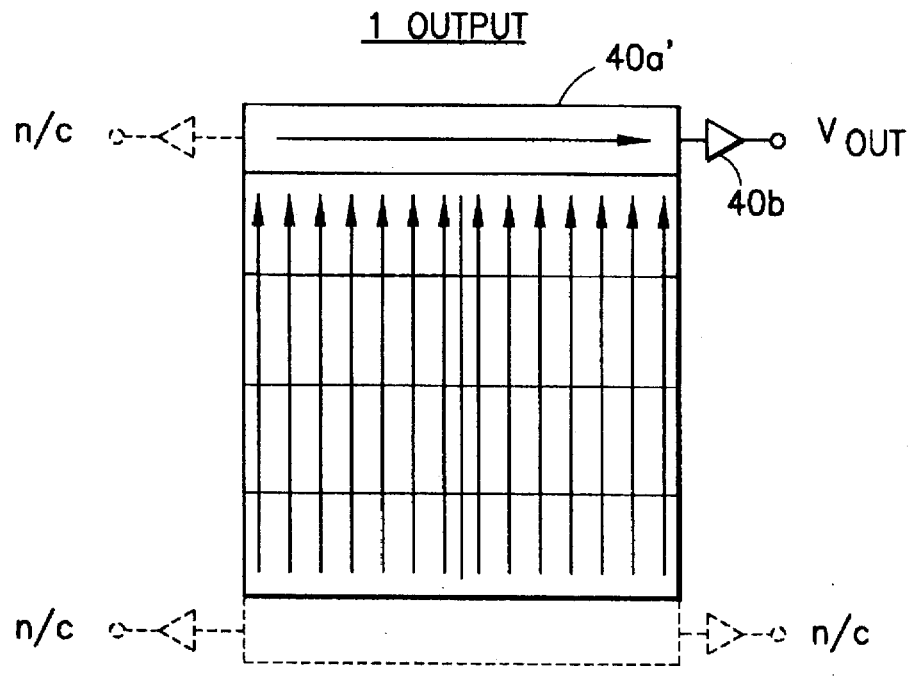
FIGS. 8A–8D each illustrate an output format that the CCD sensor chip of FIG. 5 is capable of providing.
Figure 8B:
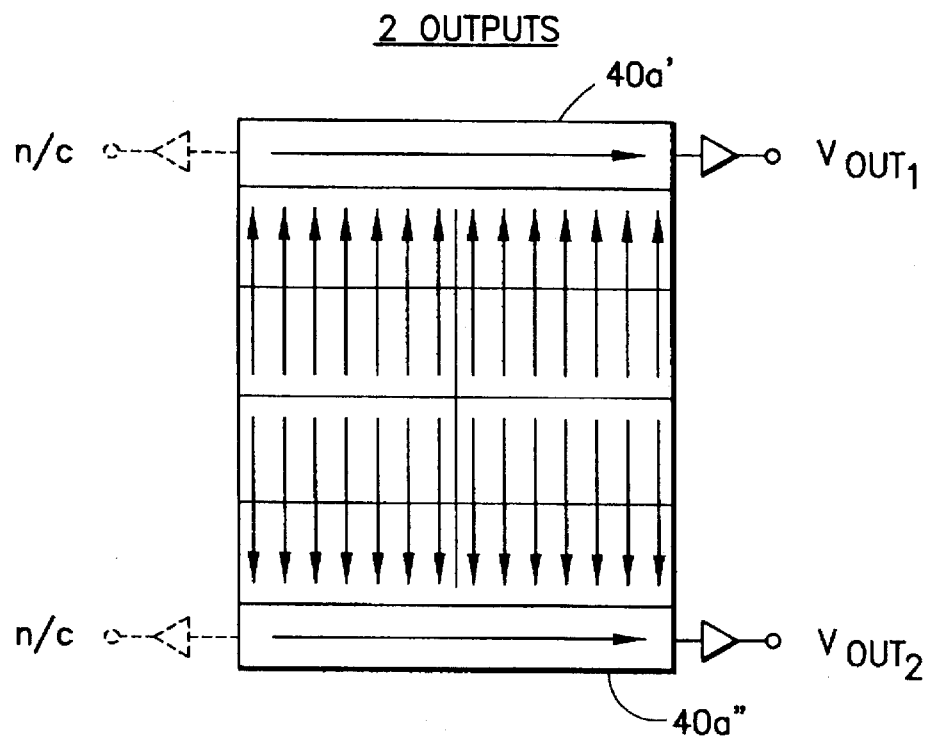
Figure 8C:
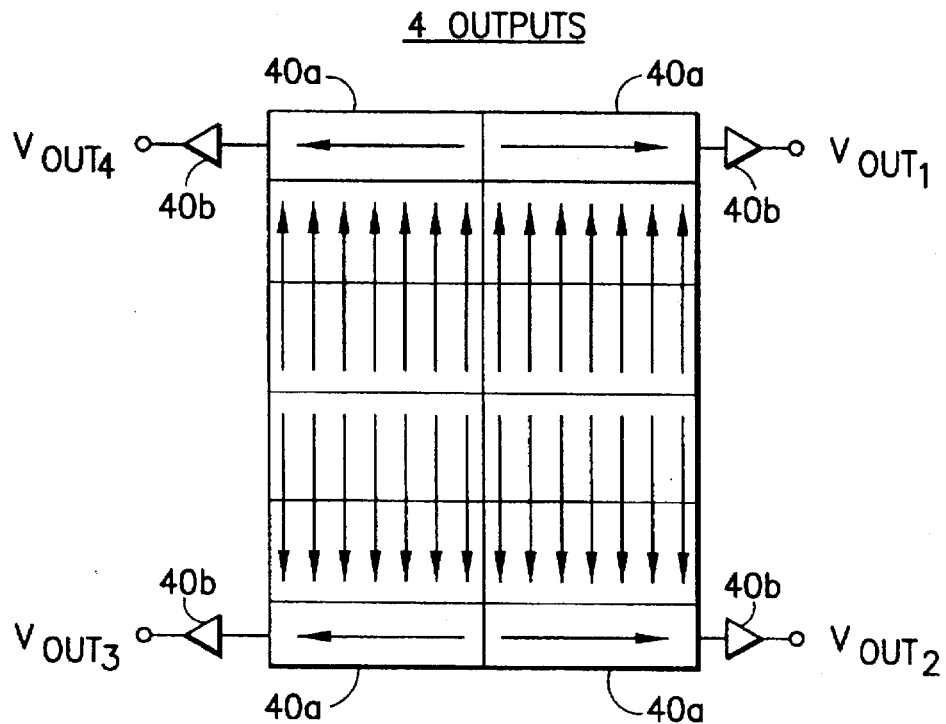
Figure 8D:
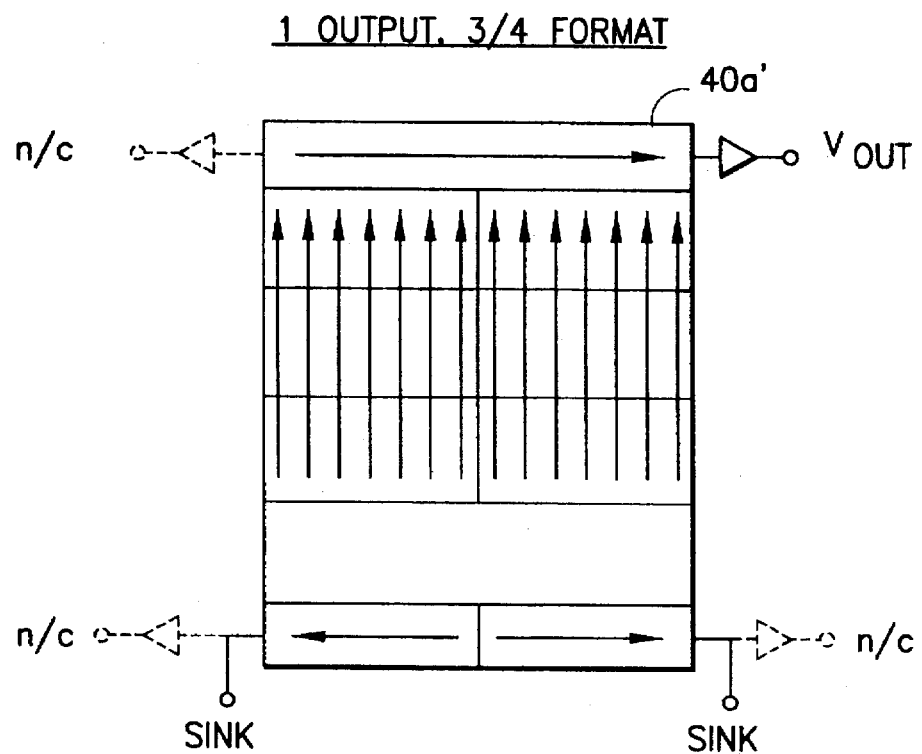

FIGS. 8A–8D illustrate a plurality of possible output configurations for the CCD chip 18a. In FIG. 8A the two upper horizontal registers 40a are combined into a single horizontal register 40a' that provides a single output to a single amplifier 40b. During operation all charge packets are vertically shifted towards the single horizontal register 40a', as is indicated by the arrows shown within the chip 18a. In FIG. 8B the two upper horizontal registers 40a are combined into the single horizontal register 40a', while the two lower horizontal registers are combined into a single horizontal register 40a". Both horizontal registers 40a' and 40a" have an associated output amplifier 40b. During operation all charge packets in the upper half of the chip are vertically shifted towards the horizontal register 40a', while all charge packets in the lower half of the chip are vertically shifted towards the horizontal register 40a". FIG. 8C is identical to the embodiment of FIG. 5. It can be noted that during operation all charge packets in each quadrant of the chip are vertically shifted towards their respective horizontal registers 40a. FIG. 8D illustrates an embodiment wherein only three quarters of the CCD pixels are used, specifically all of the upper two quadrants and half of each of the lower two quadrants. The readout technique is similar to that illustrated for FIG. 8A, while the outputs of the lower horizontal registers 40a are tied to current sinks.

The various embodiments shown in FIGS. 8A–8D can each be selected during operation by controlling the clock signals and thus configuring the CCD chip 18a as required.

Figure 7:
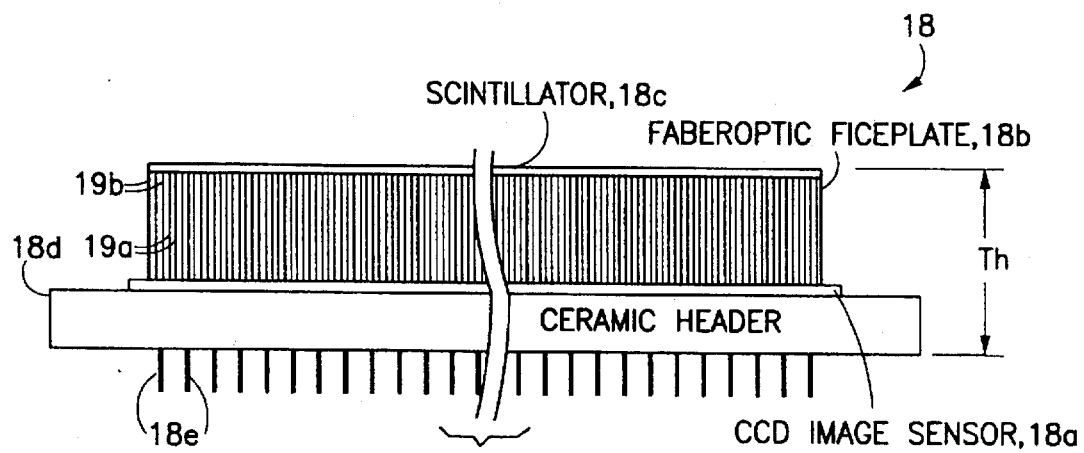
FIG. 7 is a cross-section view, not to scale, of the CCD sensor chip of FIG. 5.

Referring now also to the cross-sectional view (not to scale) of FIG. 7, the CCD sensor chip 18a is coupled to an x-ray sensitive scintillator screen 18c via the fiber optic faceplate 18b which also provides x-ray attenuation, thereby minimizing direct x-ray excitation in the CCD sensor chip 18a. Direct excitation of the CCD sensor chip 18a is preferably avoided in that it degrades image quality, and may also reduce the useful life of the CCD sensor chip. The sensor chip 18a is mounted to a header 18d which provides I/O pins 18e in a conventional fashion. The thickness (Th) of CCD assembly 18 (ignoring the pins 18e) is approximately 8 mm, thus providing a low profile unit that is suitable for enclosing within a standard size x-ray film cassette.

The fiber optic faceplate 18b is preferably cut on a bias (e.g., 6°–7°) so that the amount of x-ray radiation is minimized which can pass through the less-attenuating matrix glass 19b that surrounds the fiber optics 19a. The fiber optic faceplate 18b further has extra-mural absorption (EMA), that is, optical attenuation in the matrix glass to minimize veiling glare from the fiber optics 19a.

Figure 6:
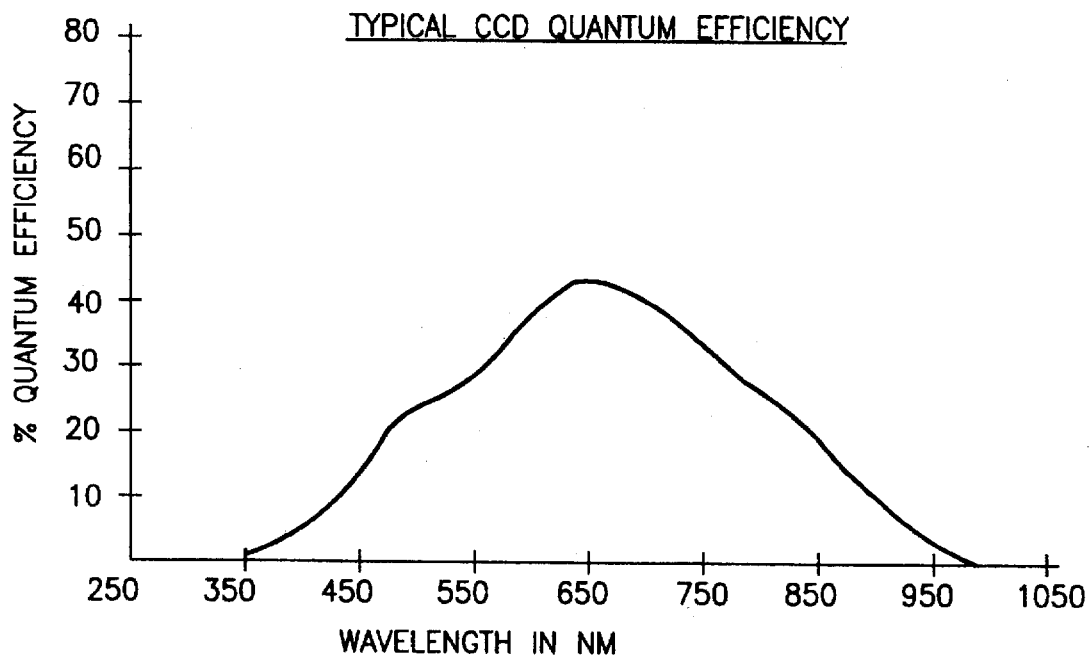
FIG. 6 is a graph that ploys CCD quantum efficiency versus wavelength.

Referring now also to FIG. 6, electromagnetic radiation that is generated in the screen 18c (typically light having wavelengths in the blue-green portion of the spectrum) is guided through the fiber optics 19a to the radiation responsive top surface of the CCD sensor chip 18a. The electromagnetic radiation is absorbed by the CCD pixels which in turn generate detectable charge packets which are subsequently read out through the horizontal register(s) 40a, 40a', 40a" and the associated amplifier(s) 40b.

The screen 18c can be a conventional x-ray responsive screen material, such as one known in the art as MIN-R that is available from Kodak. In general, the screen 18c is preferably comprised of one or more high efficiency x-ray phosphor materials, such as $GdOS:Tb(III)$, $LaOS:Tb(III)$, $LaOBr:Tb(III)$, $LaOBr:Tm(III)$, and $Ba(F,Cl)_2:Eu(II)$.

The screen 18c, fiber optic faceplate 18b, and CCD sensor chip 18a are bonded together with a conventional transparent optical cement to form the SFOCCD assembly 18. Due to the relatively small overall thickness of the SFOCCD assembly 18, the cassette 10 enclosing the SFOCCD assembly 18 and support electronics 20 can have the approximate dimensions of 10.5×7.7×0.6 inches, and is thus form and fit compatible with conventional film-based cassettes of a type illustrated in FIG. 1.

Figure 4:
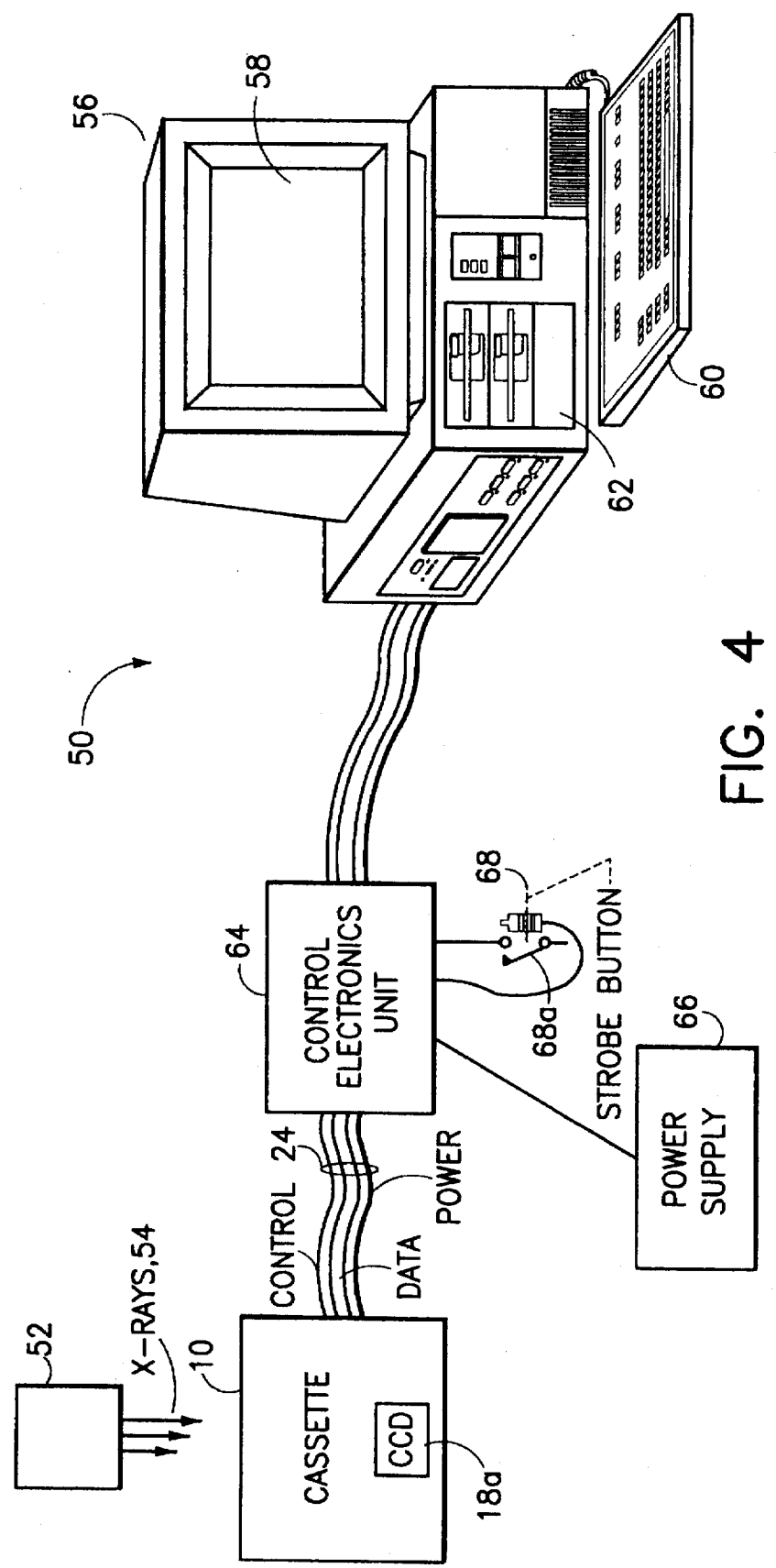
FIG. 4 is a block diagram of an x-ray system in accordance with this invention.

FIG. 4 is a block diagram of a portion of an x-ray system 50 in accordance with this invention. Although illustrated in the context of an x-ray system used for a mammography application, including stereotactic needle core biopsy, pre-operative localization, and spot view mammography applications, it should be realized that the x-ray system 50 using the novel electronic cassette 10 of this invention is capable of other uses, including industrial inspection, process control, and a variety of medical x-ray applications.

A conventional x-ray machine 52 generates an x-ray beam 54 which passes through an object being x-rayed to the cassette 10. A portion of those x-rays that are not absorbed within the object are converted to light in the screen 18c, the light is guided through the bias cut fiber optic faceplate 18b, and is detected by the CCD sensor chip 18a. The CCD pixel image data is read-out and provided through the cable 24 to a data processor, such as a PC or a workstation 56. The PC 56 includes a high resolution display 58, a keyboard 60, and an optional high capacity digital image recorder 62 used for archival and playback purposes. The PC 56 preferably executes suitable image processing software for displaying the CCD-generated image. The PC 56 includes a conventional frame grabber (FG) that is capable of capturing and storing images. Programs for digitally enhancing the image are provided as required by the operator or radiologist. Image zooming and other image manipulation functions are also provided as required.

In accordance with this invention there are provided a number of features to facilitate the operation, testing, and remote configuration of the CCD chip 18a. These functions are initiated and controlled, in one embodiment, by a CCD control electronics unit (CEU) 64 that is shown in FIG. 4. The CEU 64 includes a connection to a power supply 66 and a strobe push-button 68. The CEU 64 routes power from the power supply 66 into the cassette 10 to power the CCD chip 18a and the associated electronic circuitry 20. Alternatively, the functionality of the CCD CEU 64 can be incorporated into the PC 56, and the cassette power supplied from the PC 56. These various aspects of the invention are now described in detail.

In x-ray medical imaging, it would be desirable to be able to verify from some remote location that the CCD chip 18a and the associated electronics 20 are functioning properly. For example, it would be desirable to remotely monitor and detect any possible degradation in the CCD transport performance and amplifier performance with prolonged usage in the x-ray environment. The teaching of this invention provides this capability in the following manner.

In the CCD chip 18a, having the serial readout registers 40a at both the top and the bottom of the array, a test pattern is electrically injected by a test pattern generator (TPG) 70 (see FIG. 11) into one of the horizontal serial registers 40a through a VRD node of one of the amplifiers. The resulting charge packets are clocked into and through the CCD array and out through another horizontal serial register 40a. The output charge packets are then digitized by the associated A/D converter 42 and output to the CCD tester 64 or PC 56 for evaluation.

A preferred test pattern is typically a burst of equal-sized charge packets in a larger field of zero charge. Charge trapping within the CCD array is detected if there is charge missing from the first charge packet, and transfer inefficiency is detected by the presence of trailing charge at the end of the burst. This type of test is readily done in the two-dimensional CCD array by the use of a checkerboard type of burst pattern.

A further aspect of this invention is the use of an automatic exposure, also referred to as a pre-scan or low-dose preview technique. This technique makes use of the binning capability of the CCD chip 18a, and involves applying a low dose of x-rays and then summing a predetermined number of resulting low-level charge packets from a selected plurality of CCD pixels. A 16×16 summation or a 100×100 summation are both suitable for use during the pre-scan. From the magnitude of the charge obtained from the summation the PC 56 is enabled to determine a maximum x-ray dose that will be required to obtain an adequate image. This avoids exposing a patient to a normal dose of x-rays, determining that the dose was inadequate, and then exposing the patient to another, possibly larger dose.

The x-ray dosage required for the pre-scan is approximately 1/(X times Y), where X is the number of pixels binned horizontally and Y is the number of pixels binned vertically within an area of interest.

Another aspect of this invention is a real-time exposure control or tracking function. In this mode of operation the horizontal serial registers 40a are clocked periodically during the exposure so as to determine an amount of signal coming into the serial registers. Based on the output signals the PC 56 predicts when the optimum exposure time is reached, and the x-ray machine 52 is then signalled to turn off at that time.

In the presently preferred embodiment of the CCD chip 18a, each stage of the serial registers 40a has roughly twice the area of a basic 30×30 micron binned imaging pixel. Furthermore, the serial registers 40a are also photosensitive in that they are not covered by metalization as in many other CCDs. Therefore, by taking an 8× horizontal summation at the amplifier 40b, there is a 16× increase in signal level. This allows the PC 56 to sample the exposure up to sixteen times during the anticipated exposure period without incurring a loss in signal-to-noise ratio (SNR). When it is determined that a sufficient amount of charge has been accumulated during the exposure, the x-ray machine is controlled to terminate the exposure.

A further aspect of this invention is referred to as variable resolution. By example, in medical x-ray imaging there is a great deal of interest in resolutions corresponding to pixel sizes ranging from 40 micrometers to 100 micrometers, in addition to interest in other pixel sizes. Therefore it is beneficial to provide a CCD image sensor with a wide range of effective pixel sizes to choose from. For example, with the CCD chip 18a having a basic pixel size of 15×15 micrometers, the PC 56 programs the CCD chip 18a to provide one of 15×15, 30×30, 45×45, 60×60, 75×75 microns, etc., output pixel sizes. Preferably the variation in pixel size is achieved by binning in the CCD chip 18a, since an improved SNR can be achieved as compared to digitally combining the pixels afterward. Using this technique a large variety of pixel sizes (and aspect ratios or geometries) can be provided on demand. By example, in addition to the plurality of exemplary square pixel sizes referred to above, the CCD chip 18a can be clocked to provide a 4 k×1 linear "pixel", or a 2 k×2 pixel, etc. This capability also enables the PC 56 to measure a finite amount of x-ray dose with a very high accuracy.

A further aspect of this invention is automatic x-ray detection. It can be appreciated that the above-described real-time exposure function can be modified to detect the beginning of the exposure. That is, while waiting for the exposure to commence, and as will be described in greater detail below, the vertical clocks are run to continuously flush out dark current. By also running the horizontal register clocks and by monitoring the output of the horizontal shift registers 40a it is possible to detect a sudden increase in signal level resulting from the onset of the exposure (typically within approximately 1 millisecond after the start of the exposure). The vertical clocks can then be immediately stopped to accumulate charge during the exposure, without experiencing any significant image degradation. At this time the horizontal clocks can be continued for performing the real time exposure control that was referred to above, and/or to detect the end of the x-ray exposure.

It should be noted that in a typical mammography application the entire CCD chip 18a is likely to be covered by the breast. As a result, there is no direct high-level x-ray signal available at the CCD chip 18a for use in detecting the start of the x-ray irradiation period. Also it is noted that the CCD charge signal for a 30×30 micrometer pixel per millisecond is only approximately 10 to 20 e-, and that at least approximately a 1000 e- signal is desired in order to make a reliable decision to stop the vertical clocks for the start of integration.

It is also noted that it is important to the high performance objective of the system that, prior to the start of integration, the dark signal be dumped from the CCD chip 18a at essentially the same rate as that of the image signal readout.

In order to achieve these goals, a "ready" mode of CCD clocking includes the steps of: (a) scanning the dark signal out of the CCD chip 18a at a normal line rate, that is, at the normal number of pixel rows per second and, in a time-sharing technique, (b) providing additional clocking of the horizontal serial register(s) 40a so that x-ray signal can be read separately from the array dark signal. For example, it is common practice to have some "after-scan" clock cycles at the end of every line scan. In accordance with this invention, and for the x-ray detection function, there are up to approximately 100 after-scan clock cycles per line. By binning the charge resulting from the after-scan clock cycles at the amplifier 40b, a large enough signal can be developed to achieve the goal of obtaining at least about 1000 e- of x-ray signal.

By example, if the normal number of horizontal clock cycles is approximately 4096 array clocks+10 after-scan clocks=4106 total clocks per line, and if these are increased to 4096+100=4196, the fractional increase is only 2%. This increase is insignificant, either in terms of any increased difficulty in providing faster clocks, or in terms of some small increase in noise level.

As was previously noted, it is preferred to operate the CCD chip 18a in an uncooled or only slightly cooled mode (such as by using a miniature fan to provide a cooling airflow over and around the SFOCCD 18). In order to avoid any unnecessary heating of the CCD chip 18a prior to the exposure and signal readout, it is desirable to have the CCD chip 18a and the associated electronics 20 in a low-power standby mode. This minimizes the dark signal and therefore the noise floor for a given readout time.

Figure 9:
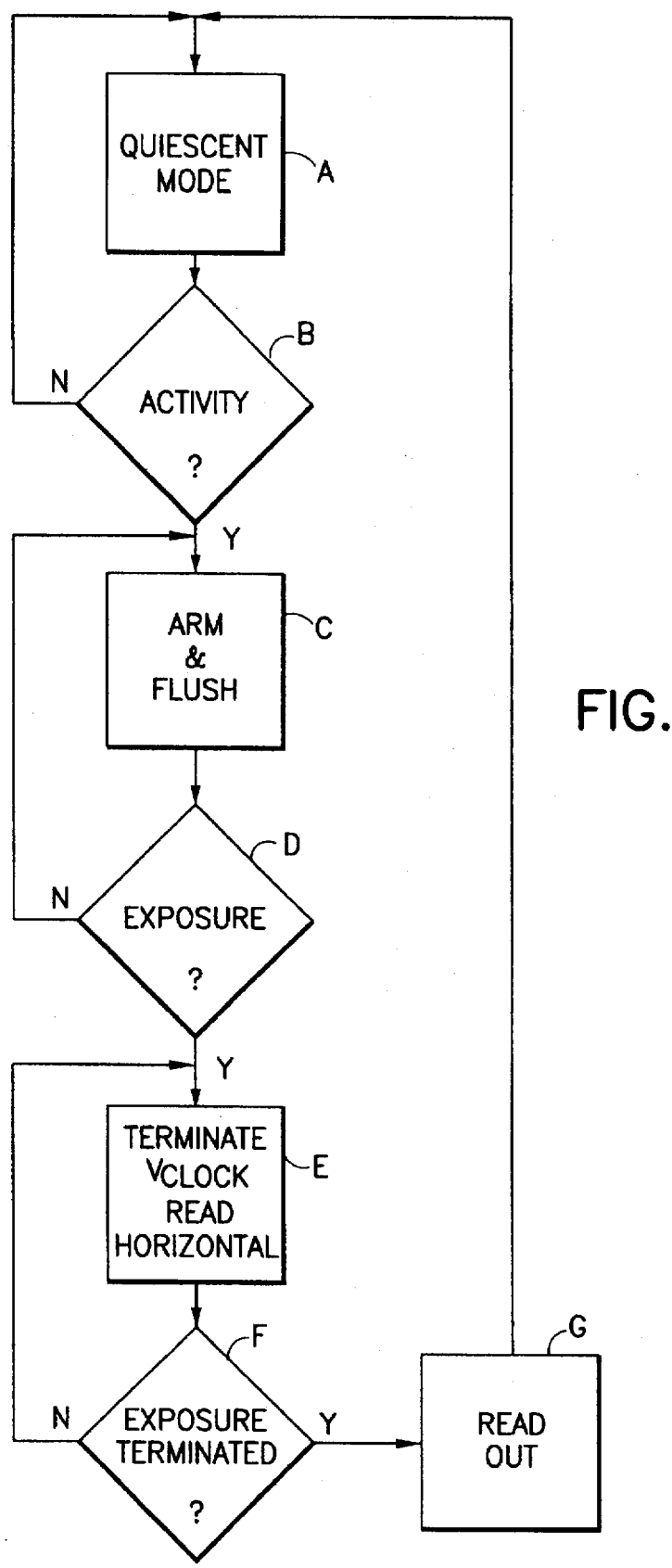
FIG. 9 is a logic flow diagram that illustrates the operation of the electronic x-ray cassette in accordance with an aspect of this invention.

Reference is now made to FIG. 9 for showing a presently preferred method of this invention that accomplishes the low-power standby mode referred to above. At block A the CCD chip 18a and associated electronics 20 are placed in a standby or quiescent mode. In this mode all unnecessary clocks are reduced in frequency or are stopped completely and, if appropriate, power supply voltages are reduced or turned off. The system remains in this state until activity is detected at block B. The detection of activity can be accomplished by providing the operator with a push button switch to indicate that an exposure will soon be taken. It is also within the scope of the invention to mount the hand-held strobe button 68 shown in FIG. 4, which is used by the operator to initiate an exposure, to a switched mounting 68a. In this manner, when the operator removes the hand-held strobe button 68 from the mounting 68a a switch is activated. The change in state of the switch is detected by the CCD CEU 64 (or PC 56) and is interpreted as a change in state of system activity (i.e., that an exposure will soon be made). It is also within the scope of this invention, and referring also to FIG. 3, to employ a proximity or other type of sensor to detect that the breast has been compressed prior to making an exposure.

Assuming now that a determination has been made at block B that activity has started, the method transitions to block C where the CCD chip 18a is armed and the dark current is flushed from the pixels. In other words, the CCD chip 18a and associated electronics 20 are brought out of the quiescent mode to a full operational status, and the vertical clocks are run so as to remove the dark current. A complete flush of the dark current may take, by example, three seconds. At block D a determination is made if the x-ray exposure has started. This can be accomplished, as was described above, by oversampling the horizontal registers during the dark current flush and then binning the over-sample readouts to determine an increase in charge that is generated by the horizontal registers 40a in response to the x-ray flux. The system loops through blocks C and D to continuously flush dark current and wait for the start of the exposure.

Assuming that the start of the exposure is detected, at block E the vertical clocks of the CCD chip 18a are immediately stopped so as to initiate the integration of charge within the individual pixels. The horizontal register clocks can continue to run so as to (1) detect an onset and a termination of the exposure, (2) to perform the automatic exposure length function that was referred to above, and/or to (3) perform the real time exposure control function. If this latter function is performed then it may not be necessary to also perform the detection of the termination of the exposure. If desired, the prescan function referred to above can also be performed. The system loops between blocks E and F until the exposure is terminated, at which time control passes to block G to readout the integrated charge that resulted from the exposure. Control then passes to block A to re-enter the low power quiescent mode until activity is once again sensed.

Figure 10:
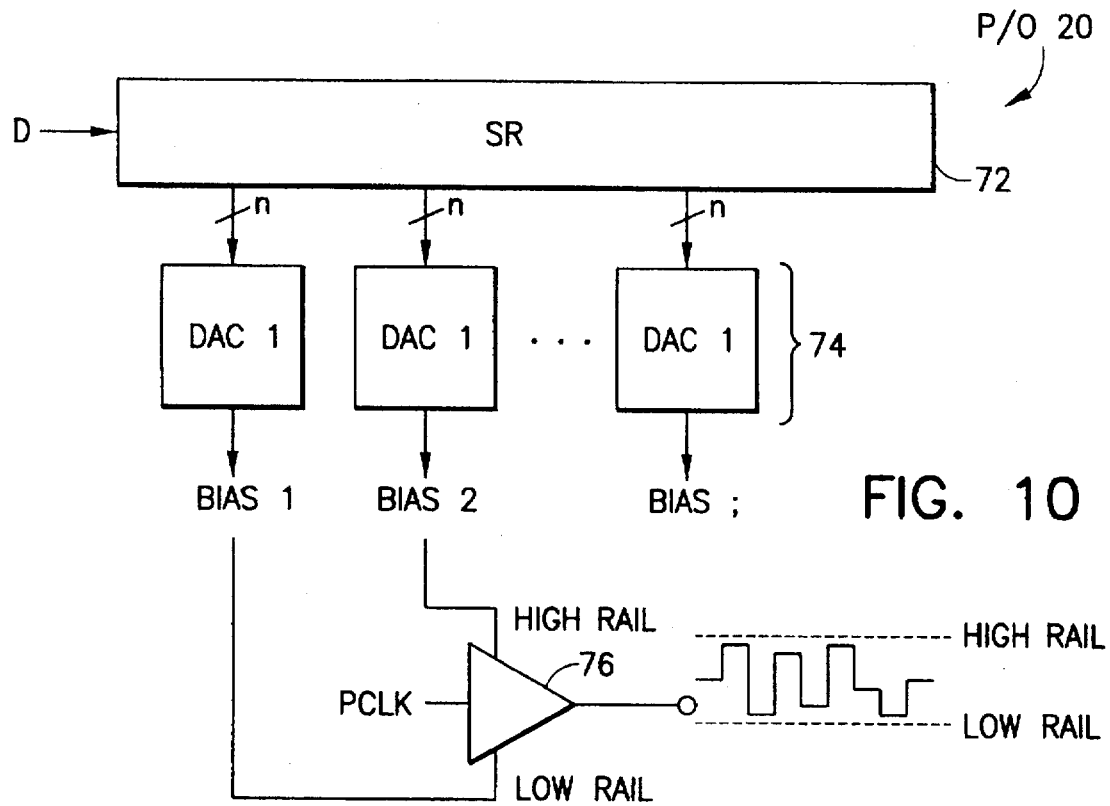
FIG. 10 is a block diagram of electronic x-ray cassette circuitry for generating clock bias potentials in accordance with this invention.
Figure 11:
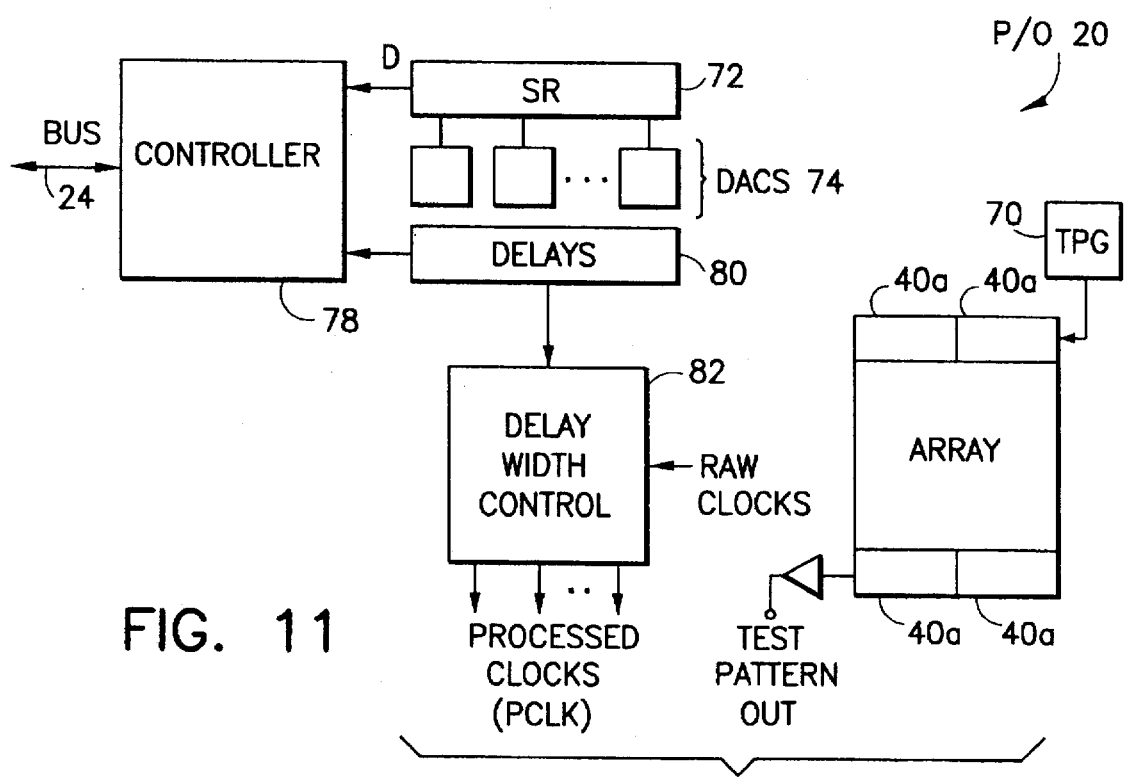
FIG. 11 is a block diagram of electronic x-ray cassette circuitry for generating variably-delayed clock signal waveforms in accordance with this invention.

A further aspect of this invention is an ability to remotely perform an automatic optimization of image quality. Referring to FIGS. 10 and 11, this function is accomplished by having clock duty cycles and levels, and also dc-bias potentials, set by digital-to-analog converters (DACs) and other circuitry. As a result, the capability is provided to remotely control bias and clock potentials and waveshapes, and to then examine the resulting output of the CCD chip 18a, such as was described previously with regard to the remote testability function. Based on the output of the CCD chip 18a for a given combination of clock and bias potentials, the PC 56 is enabled to determine optimal settings for such parameters as: (a) lowest dark signal (optimum MPP (multi-pinned phase)), (b) best vertical transfer efficiency, (c) best horizontal transfer efficiency, etc. In this regard it should be realized that the PC 56 need not be in the same location as the x-ray machine 52. In fact, the PC 56 could be located a considerable distance away, such that the data links between the PC 56 and the cassette 10 are conveyed, by example, telephonically though a modem connection.

Referring first to FIG. 10 there is shown a portion of the support electronics 20 in accordance with this aspect of the invention. A shift register 72 is provided for receiving a data signal (D) from the PC 56, via a local controller 78 as shown in FIG. 11. In this embodiment of the invention a total of 32 bias signals are generated, each having, by example, 12 bits of resolution. At the outputs of the shift register 72 a plurality (e.g., 32) DACs (DACs1-i) 74 are connected for receiving 12-bit inputs. The analog outputs of the 32 DACs 74 provide the 32 bias potentials. Some of these bias potentials are used for setting the high and low excursions of the required clock signals (10 clocks total requiring 20 clock bias potentials). One of these clock circuits is shown as an amplifier 76 that receives a processed clock (PCLK) signal from a delay width controller 82 shown in FIG. 11. Two bias potentials (e.g., BIAS1 and BIAS2) are connected to the high and low power rails of the amplifier 76. By controllably adjusting the magnitudes of BIAS1 and BIAS2 the clock excursions can be correspondingly controlled. Other bias potentials are provided to the CCD chip 18a and the amplifiers 40b as required. By example, the VDD input to the amplifier 40b in FIG. 5 is connected to a diode within the CCD chip 18a. By controlling the conduction of this diode via the magnitude of VDD the image readout is also controlled.

In FIG. 11 the local controller 78 is shown connected to the bus 24. The local controller 78 outputs the data signal (D) to the DACs 74 via the shift register 72, and also to a delay shift register 80. The output of the delay shift register 80 is provided to the above mentioned delay width controller 82 for specifying the pulse widths or duty cycles of the processed clock signals (PCLKs). The delay width controller receives "raw" clock signals (e.g., 50 MHz) from a clock source that is generated either within the cassette 10 or externally and received through the cable 24.

In operation, and by example, the PC 56 can optimize the dark current by adjusting the bias potentials until a desired dark current level is reached. In this regard the PC 56 obtains an optimum MPP mode by controllably decreasing the various clock signal low rails while continuously monitoring the dark current so as to set the dark current at a minimum value. It can be appreciated that this task would be tedious and time consuming if done manually, and furthermore would require the attention of a skilled technician or engineer.

After the optimum bias values are determined by the PC 56, these values can be stored and later recalled and downloaded via the cable 24 to the optimization circuitry shown in FIGS. 10 and 11. As was previously noted, the PC 56 can be remotely located from the x-ray system and cassette 10. Alternatively, the data representing the optimum operating parameters for the CCD system can be stored within a non-volatile memory within the cassette 1, and then subsequently recalled by the local controller 78 for setting the DACs 74 and/or delay width controller 82 accordingly.

Based on the foregoing it should be noted that this invention provides a closed loop capability to remotely test, diagnose and/or calibrate a CCD-based x-ray image sensor, wherein an external controller is enabled to controllably stimulate the CCD-system, read-out the resulting signals, and then vary the stimulation to obtain a desired output. For example, clock biases and delays can be individually adjusted, a test pattern introduced via the TPG 70, and the resulting output analyzed to determine a correct setting for the large number of variables (clock duty cycles, clock biases, CCD-biases, etc.) which must be considered in order to optimize the image-gathering capability of the SFOCCD 18.

The Appendix sets forth a number of exemplary CCD and support electronics operating parameters and their typical ranges. It is within the scope of this invention to provide for remote programmability of one or more of these operating parameters. It should be noted that the various potentials can in practice be driven through a range of, by example, ±25 V, with clock rates up to, by example, 50 MHz. In this manner it is possible to compensate for process variations between CCDs. Furthermore, and for a multiple CCD embodiment, the teaching of this invention enables each of the CCDs to be separately adjusted and optimized.

By example, offset compensation can also be accomplished to accommodate the change in the level of the output DC of the video signal as a function of CCD device, temperature and time. One preferred method for performing offset compensation is as follows. First, the ADC clocks are changed to sample the reset level on both legs of the ADC. Next, the front end offset (FEO) is changed to minimize the offset reading from the ADC. The ADC clocks are then changed to sample the reset and the reference shelf potentials. These readings are then minimized by again varying the front end offset. Finally, the ADC clocks are restored to a normal operating mode. In accordance with an aspect of this invention, all of these functions can be performed remotely by programming the various CCD support electronics and circuitry.

Thus, while the invention has been particularly shown and described with respect to presently preferred embodiments thereof, it will be understood by those skilled in the art that changes in form and details may be made therein without departing from the scope and spirit of the invention. By example, the various dimensions, lay-out, clocks and clock frequencies referred to above are exemplary of but one suitable CCD device for practicing this invention, and are not to be considered as a limitation on the practice of this invention.

As such, the scope of the teaching of this invention is not intended to be limited to only the embodiments that have been expressly disclosed and illustrated, but instead the teaching of this invention should be read as being commensurate with the scope of the claims that follow.

| APPENDIX | | | | | |
|---|---|---|---|---|---|
| | | RANGE | | | |
| SYMBOL | CHARACTERISTIC | MIN | TYP | MAX | UNITS |
| DC VOLTAGES RANGES | | | | | |
| VDD | Output Amplifier Drain Supply Voltage | 15.0 | 22.0 | 25.0 | V |
| VRD | Output Reset Drain Supply Voltages | 10.0 | 12.0 | 20.0 | V |
| VOG | Output DC Gate Voltages | 0.0 | 0.5 | 5.0 | V |
| VRT | Amplifier Signal Ground | 0.0 | 3.0 | 5.0 | V |
| VSS | Substrate Bias | | 0.0 | | V |
| CLOCK BIASES RANGES | | | | | |
| VØH HIGH | Horizontal Transport Gate HIGH | 2.0 | 5.0 | 8.0 | V |
| VØSG HIGH | Output Summing Gate HIGH | 2.0 | 5.0 | 8.0 | V |
| VØR HIGH | Reset Gate HIGH | 5.0 | 8.0 | 15.0 | V |
| VØV HIGH | Vertical Transport Gate HIGH | 0.0 | 3.0 | 5.0 | V |
| VØVTG HIGH | Vertical Transfer Gate HIGH | 0.0 | 3.0 | 5.0 | V |
| VØH LOW | Horizontal Transport Gate LOW | −8.0 | −5.0 | −2.0 | V |
| VØSG LOW | Output Summing Gate LOW | −8.0 | −5.0 | −2.0 | V |
| VØR LOW | Reset Gate LOW | −5.0 | 0.0 | 5.0 | V |

-continued

APPENDIX

| SYMBOL | CHARACTERISTIC | RANGE MIN | TYP | MAX | UNITS |
|---|---|---|---|---|---|
| VØV LOW | Vertical Transport Gate LOW | −10.0 | −8.0 | −5.0 | V |
| VØVTG LOW | Vertical Transfer Gate LOW | −10.0 | −8.0 | −5.0 | V |
| ELECTRONICS SYSTEM CONTROLS | | | | | |
| FEG | Front End Gain | 1:1 | | 25:1 | |
| FEO | Front End Offset | 0 | | 14 | V |
| BEG | Back End Gain | 1:1 | | 25:1 | |
| BEO | Back End Offset | 0 | | 5 | V |
| ADC_DLY | ADC Clock Delay | 0 | | 512 | n.s. |
| RST_DLY | Reset Shelf Sample Delay | 0 | | 512 | n.s. |
| PXL_DLY | Pixel Sample Pulse Delay | 0 | | 512 | n.s. |
| OVR_SMP | ADC Pixel Oversampling | 1 | | 4 | times |

What is claimed is:

1. A method for operating an x-ray system, comprising the steps of:

providing a solid state x-ray image sensor system within an enclosure, the sensor system comprising a solid state radiation detector, the sensor system being electrically coupled to a controller;

outputting data from the controller to the solid state x-ray image sensor system, the data specifying at least one operational parameter of the image sensor system including at least one of a duty cycle of at least one clock signal, a level of at least one clock signal, and a bias potential;

monitoring, from the controller, an output of the image sensor system when operating with the at least one operational parameter; and varying the at least one operational parameter and executing the steps of outputting data and monitoring until the output of the image sensor system is in agreement with a desired output.

2. A method as set forth in claim 1 wherein the step of monitoring includes a step of reading out a dark signal from the solid state radiation detector and outputting a magnitude of the dark signal to the controller.

3. A method for operating an x-ray system, comprising the steps of:

providing a solid state x-ray image sensor system within an enclosure, the sensor system comprising a solid state radiation detector, the sensor system being electrically coupled to a controller;

outputting data from the controller to the solid state x-ray image sensor system, the data specifying at least one operational parameter of the image sensor system including at least one of a duty cycle of at least one clock signal, a level of at least one clock signal, and a bias potential;

monitoring, from the controller, an output of the image sensor system when operating with the at least one operational parameter; and varying the at least one operational parameter and executing the steps of outputting data and monitoring until the output of the image sensor system is in agreement with a desired output;

wherein the step of monitoring includes a generating a test pattern, injecting the test pattern into the solid state radiation detector, clocking the injected test pattern through the solid state radiation detector, reading the test pattern out of solid state radiation detector, and outputting a magnitude of the read-out test pattern to the controller.

4. A method as set forth in claim 1 and further comprising the steps of:

storing data representing one or more operating parameters that are determined provide the desired output from the image sensor system; and subsequently using the stored data for re-establishing the operating parameters to provide the desired output.

5. A method as set forth in claim 1 wherein the solid state radiation detector is comprised of a CCD that is optically coupled to an x-ray responsive scintillating material.

6. A method for operating an x-ray system, comprising the steps of:

providing a solid state x-ray image sensor system within an enclosure, the sensor system comprising a CCD-based radiation detector comprised of a plurality of lines of radiation responsive pixels, the sensor system being electrically coupled to a controller; and detecting an occurrence of a start of an x-ray exposure by the steps of:

clocking the CCD-based radiation detector to read out a dark signal in a line-by-line format, the step of clocking including a step of generating more clock pulses than there are pixels within a line for over-scanning a radiation-responsive CCD read-out register with the additional clock pulses;

summing charge packets output from the read-out register in response to the additional clock pulses; and monitoring the summed charge packets to detect an increase in magnitude in the summed charge packets, the increase in magnitude being indicative of an occurrence of a start of an x-ray exposure.

7. A method as set forth in claim 6, wherein the step of clocking includes a step of clocking vertical registers and at least one horizontal read-out register of the CCD-based radiation detector, and further including a step of terminating the clocking of the vertical registers when the occurrence of the start of the x-ray exposure is indicated.

8. A method as set forth in claim 7, and further comprising the steps of:

continuing to clock the at least one horizontal register during the x-ray exposure for periodically reading out accumulated charge packets therefrom;

summing magnitudes of the read-out charge packets;

comparing the summed magnitudes to a reference magnitude; and terminating the x-ray exposure when the summed magnitudes are equal to or greater than the reference magnitude.

9. A method for operating an x-ray system, comprising the steps of:
  providing a solid state x-ray image sensor system within an enclosure, the sensor system comprising a CCD-based radiation detector comprised of a plurality of radiation responsive pixels, the sensor system being electrically coupled to a controller;
  placing the image sensor system into a low-power state;
  detecting an occurrence of an activity that is a precursor to making an x-ray exposure;
  placing the image sensor system into a higher power operational state;
  flushing dark signal from the pixels of the CCD-based radiation detector while monitoring for a start of an x-ray exposure;
  at the start of the x-ray exposure, terminating the flushing of dark signal and accumulating charge within the pixels; and
  at a termination of x-ray exposure, reading out the accumulated charge and forming an image therefrom.

10. A method as set forth in claim 9 wherein the step of flushing dark signal includes the steps of:
  clocking the CCD-based radiation detector to read out the dark signal in a line-by-line format, the step of clocking including a step of generating more clock pulses than there are pixels within a line for over-scanning a radiation-responsive CCD read-out register with the additional clock pulses;
  summing charge packets output from the read-out register in response to the additional clock pulses; and
  monitoring the summed charge packets to detect an increase in magnitude in the summed charge packets, the increase in magnitude being indicative of an occurrence of a start of the x-ray exposure.

11. A method as set forth in claim 10, wherein the step of clocking includes a step of clocking vertical registers and at least one horizontal read-out register of the CCD-based radiation detector, and further including a step of terminating the clocking of the vertical registers when the occurrence of the start of the x-ray exposure is indicated.

12. A method as set forth in claim 11, and further comprising the steps of:
  continuing to clock the at least one horizontal register during the x-ray exposure for periodically reading out accumulated charge packets therefrom;
  summing magnitudes of the read-out charge packets;
  comparing the summed magnitudes to a reference magnitude; and
  terminating the x-ray exposure when the summed magnitudes are equal to or greater than the reference magnitude.

13. A method as set forth in claim 9 wherein the step of reading-out includes a step of combining charge packets from adjacent pixels within an area having a controller-selected aspect ratio.

14. An x-ray imaging system, comprising:
  a controller;
  an x-ray image sensor system electrically coupled to said controller;
  means for transferring data from said controller to said x-ray image sensor system, the data specifying at least one of a voltage potential and a timing characteristic;
  said x-ray image sensor system comprising means for transforming said transferred data into a change in state of at least one of said voltage potential and said timing characteristic; and
  said controller comprising means for monitoring an output of said x-ray image sensor system, when operating with said at least one of said voltage potential and said timing characteristic, and for varying the data specifying said at least one of said voltage potential and said timing characteristic in accordance with the monitored output.

15. An x-ray imaging system as set forth in claim 14, wherein said monitoring means is comprised of means for reading out a dark signal from a solid state radiation detector and for outputting a magnitude of the dark signal to said controller.

16. An x-ray imaging system, comprising:
  a controller;
  an x-ray image sensor system electrically coupled to said controller;
  means for transferring data from said controller to said x-ray image sensor system, the data specifying at least one of a voltage potential and a timing characteristic;
  said x-ray image sensor system comprising means for transforming said transferred data into a change in state of at least one of said voltage potential and said timing characteristic; and
  said controller comprising means for monitoring an output of said x-ray image sensor system, when operating with said at least one of said voltage potential and said timing characteristic, and for varying the data specifying said at least one of said voltage potential and said timing characteristic in accordance with the monitored output;
  wherein said monitoring means is comprised of:
  means for generating a test pattern and for injecting the generated test pattern into a solid state radiation detector;
  and wherein said x-ray image sensor system is comprised of means for clocking the injected test pattern through said solid state radiation detector, for reading the test pattern out of said solid state radiation detector, and for outputting a magnitude of the read-out test pattern to said controller.

17. An x-ray imaging system as set forth in claim 14, wherein said controller is further comprised of:
  means for storing data representing at least one operating parameter that is predetermined to provide a desired operation state of said x-ray image sensor system; and
  means for reading out the stored data and for transferring the stored data to said x-ray image sensor system for establishing the desired operational state.

18. An x-ray imaging system as set forth in claim 14, wherein said x-ray image sensor system is comprised of at least one CCD that is optically coupled to an x-ray responsive light emitting material.

19. An x-ray sensor, comprising:
  a two dimensional array of charge coupled devices;
  a first readout register disposed along one edge of said array; and
  a second readout register disposed along an opposite edge of said array;
  wherein said first and second readout registers are each electrically configurable for operation as one readout register that transports array output signals in one direction or as two smaller readout registers that transport array output signals in two directions.

20. A method for flushing dark current from an x-ray sensor, comprising steps of:

providing a two dimensional array of charge coupled devices, the array being provided to have a first readout register disposed along one edge of the array and a second readout register disposed along an opposite edge of the array;

prior to an occurrence of an X-ray exposure detecting an occurrence of an activity that is a precursor to making an x-ray exposure and, clocking both the first and second readout registers so as to remove dark current from the array;

at the start of an X-ray exposure, terminating the clocking of both the first and second readout registers; and after the occurrence of the X-ray exposure, clocking both the first and second readout registers so as to remove X-ray image signal current from the array.

* * * * *